(12) United States Patent
Marshall et al.

(10) Patent No.: US 7,563,252 B2
(45) Date of Patent: Jul. 21, 2009

(54) AUTOMATIC PEN-TYPE INJECTOR

(75) Inventors: Jeremy Marshall, Oxford (GB); Steven Mark Guy Rolfe, Oxon (GB)

(73) Assignee: Owen Mumford Limited, Woodstock, Oxfordshire (GB)

( * ) Notice: Subject to any disclaimer, the term of this patent is extended or adjusted under 35 U.S.C. 154(b) by 132 days.

(21) Appl. No.: 10/563,318

(22) PCT Filed: Jul. 5, 2004

(86) PCT No.: PCT/GB2004/002903

§ 371 (c)(1),
(2), (4) Date: Jan. 4, 2006

(87) PCT Pub. No.: WO2005/002653

PCT Pub. Date: Jan. 13, 2005

(65) Prior Publication Data

US 2006/0167413 A1    Jul. 27, 2006

(30) Foreign Application Priority Data

Jul. 4, 2003    (GB) ................................ 0315600.7

(51) Int. Cl.
*A61M 5/00* (2006.01)
(52) U.S. Cl. .................................................. 604/187
(58) Field of Classification Search .............. 604/23, 604/181, 187, 188, 110, 198
See application file for complete search history.

(56) References Cited

U.S. PATENT DOCUMENTS

| | | | |
|---|---|---|---|
| 4,553,553 A | 11/1985 | Bayer et al. | |
| 4,943,282 A | 7/1990 | Hamilton et al. | |
| 5,114,406 A * | 5/1992 | Gabriel et al. | 604/136 |
| 5,207,646 A | 5/1993 | Brunel | |
| 5,320,609 A * | 6/1994 | Haber et al. | 604/135 |
| 5,666,966 A * | 9/1997 | Horie et al. | 600/573 |
| 6,050,977 A * | 4/2000 | Adams | 604/195 |
| 6,494,863 B1 * | 12/2002 | Shaw et al. | 604/110 |
| 6,558,357 B1 * | 5/2003 | Hoeck | 604/195 |
| 6,620,137 B2 * | 9/2003 | Kirchhofer et al. | 604/218 |
| 6,989,001 B2 * | 1/2006 | Chen | 604/110 |
| 7,278,986 B1 * | 10/2007 | Frost | 604/195 |
| 7,361,160 B2 * | 4/2008 | Hommann et al. | 604/198 |

FOREIGN PATENT DOCUMENTS

EP    0 516 473    12/1992

* cited by examiner

*Primary Examiner*—Kevin C Sirmons
*Assistant Examiner*—Michael J Anderson
(74) *Attorney, Agent, or Firm*—Young & Thompson

(57) ABSTRACT

A syringe (1) is moved bodily forward by a plunger (7) (after release of a spring 8) by acting through an O-ring pressing onto an enlarged head (16) of a syringe container (3), in order to expose the needle (5) of the syringe before the plunger acts on a plug (4) within the syringe to cause the liquid to be ejected through the needle. There is, therefore, a two-step movement of the plunger, firstly together with the syringe through the medium of the O-ring, and secondly within the syringe container to force the plug forward, when a ledge (12) on the syringe container (3) is arrested by a stop (14), whereupon the frictional force between the plunger and the O-ring is relieved so that the plunger slides forward through the O-ring.

7 Claims, 4 Drawing Sheets

AUTOMATIC PEN-TYPE INJECTOR

Figure 1:
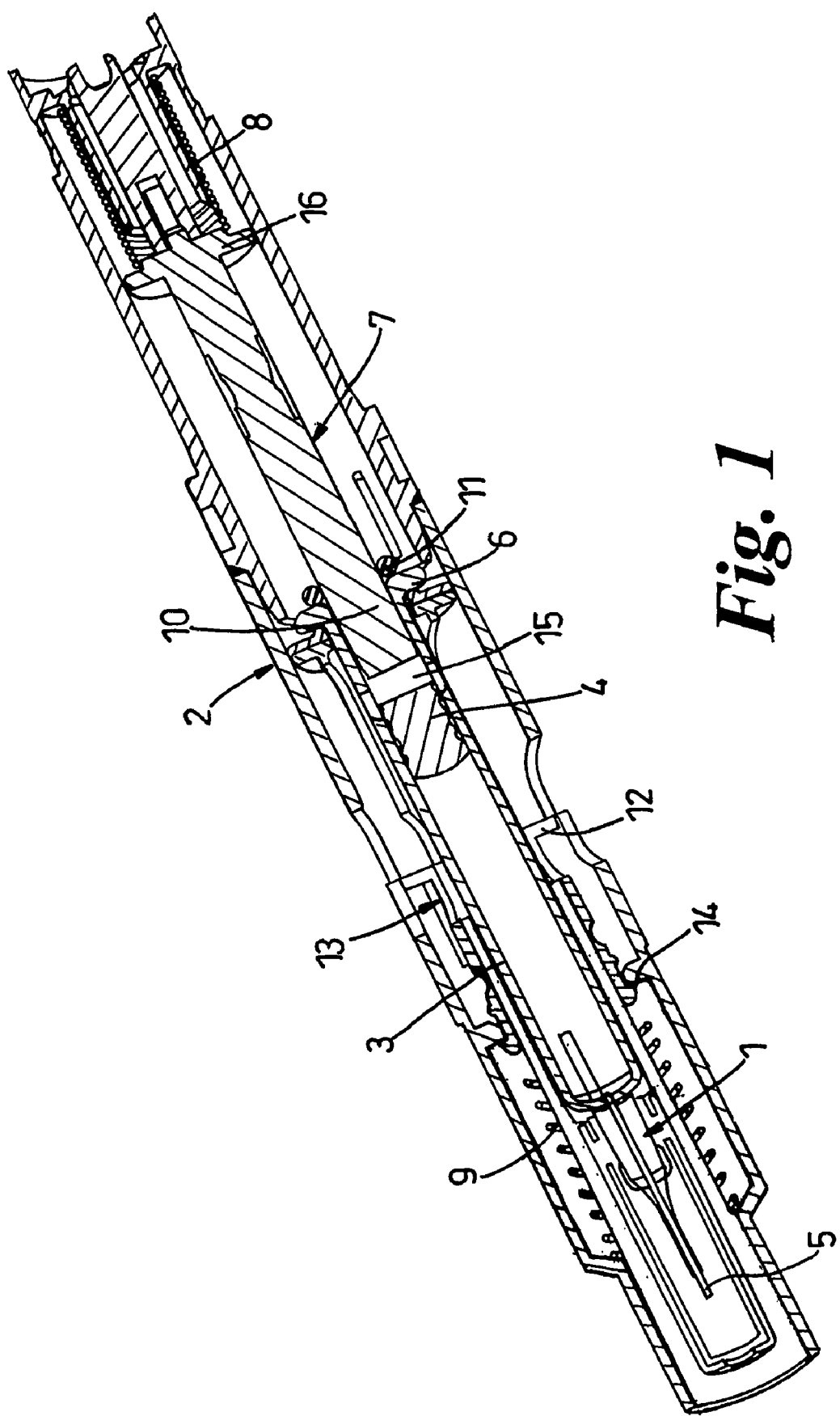

There are various forms of automatic injection device which when operated cause the needle of a syringe to be moved forwardly so that it projects from a protective housing prior to actuation of the syringe to express a dose of liquid through the needle. It is important to try to ensure that the syringe is moved bodily forward to expose the needle before the liquid charge is pressurised so that dribbling from the needle does not occur before the actual injection takes place. It is an object of this invention to provide a mechanism which operates in this desired manner.

According to the invention there is provided an injection device for causing a dose of liquid to be ejected from the needle at one end of a syringe located within a housing of the device, the syringe being movable by a plunger, upon release of an actuating bias member at one end of the housing, to move the syringe, from a first position wherein the needle is shrouded by the housing, to a second position wherein the needle projects from the other end of the housing, the plunger having its free end positioned within the other end of a container of the syringe and carrying a surrounding and gripping flexible O-ring which rests against an enlarged head of the other end of the syringe, such that a primary movement of the plunger, under the bias of the actuating bias member, will transmit a frictional force to the O-ring with the result that the syringe container is moved by the O-ring from said first to said second position, whereupon arresting of further movement of the syringe results in the frictional grip between the plunger and the O-ring being partially released, thus enabling the plunger to move by a secondary movement, into the syringe container, into contact with and to act upon a plug to compress the liquid within the syringe and cause expression of the liquid through the syringe needle.

Thus, with this device, the syringe is moved bodily forward, by the action of the O-ring onto the enlarged head of the syringe container, in order to expose the needle before the plunger acts on the plug within the syringe to cause the liquid to be ejected through the needle. There is, therefore, a two-step movement of the plunger, firstly together with the syringe through the medium of the O-ring, and secondly within the syringe container to force the plug forward when the frictional force between the plunger and the O-ring is relieved and the plunger slides forward through the O-ring.

In a preferred embodiment, the structure will be modified to include a pressure maintaining bias member which is positioned between a head of the plunger and the O-ring to enable pressure to be maintained by the O-ring onto the head of the syringe container during the secondary movement of the plunger. This ensures that the plunger acts to a greater extent to press the O-ring against the head of the syringe during the secondary stage of movement of the plunger, so that the syringe itself does not tend to move back into the housing during this secondary stage of movement.

Preferably, there will be a return bias member bias member acting between the syringe housing and the other end of the syringe container to hold the syringe retracted within the housing until the actuating bias member is released. This return bias member holds the syringe retracted within the housing until such time as the actuating bias member is released.

One or more of the bias members provided within the housing can be in the form of a coil spring.

Figure 2:
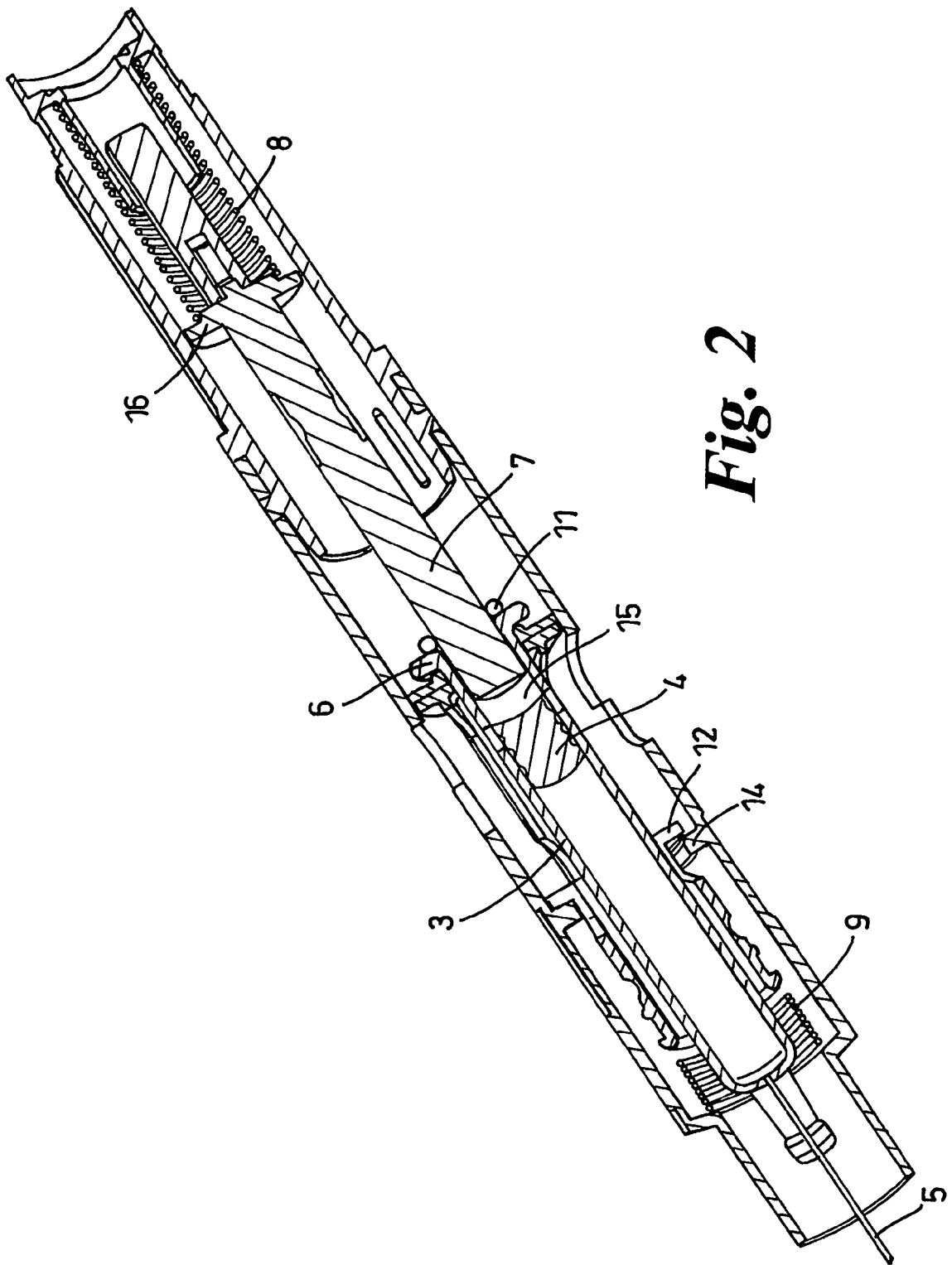
Figure 3:
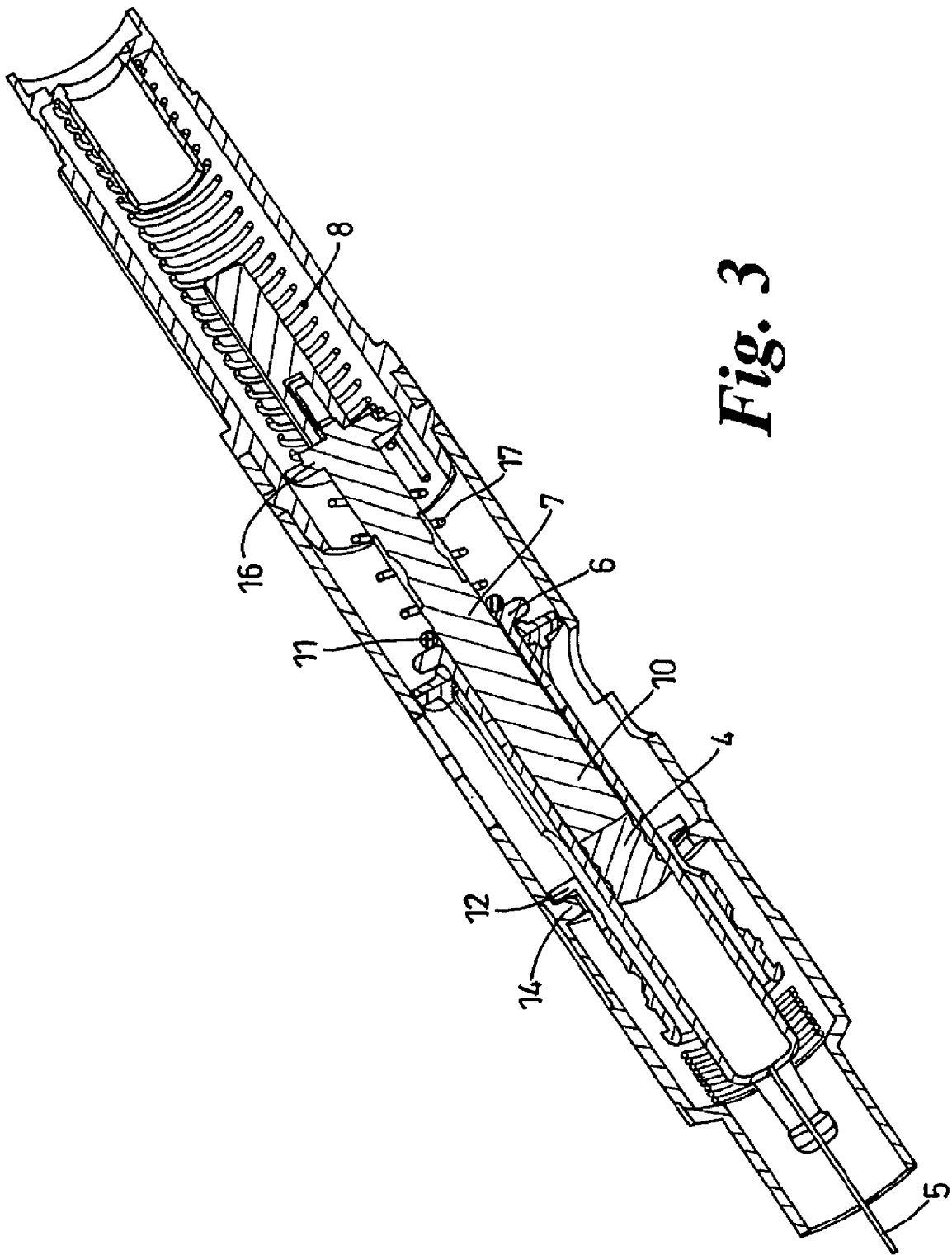
Figure 4:
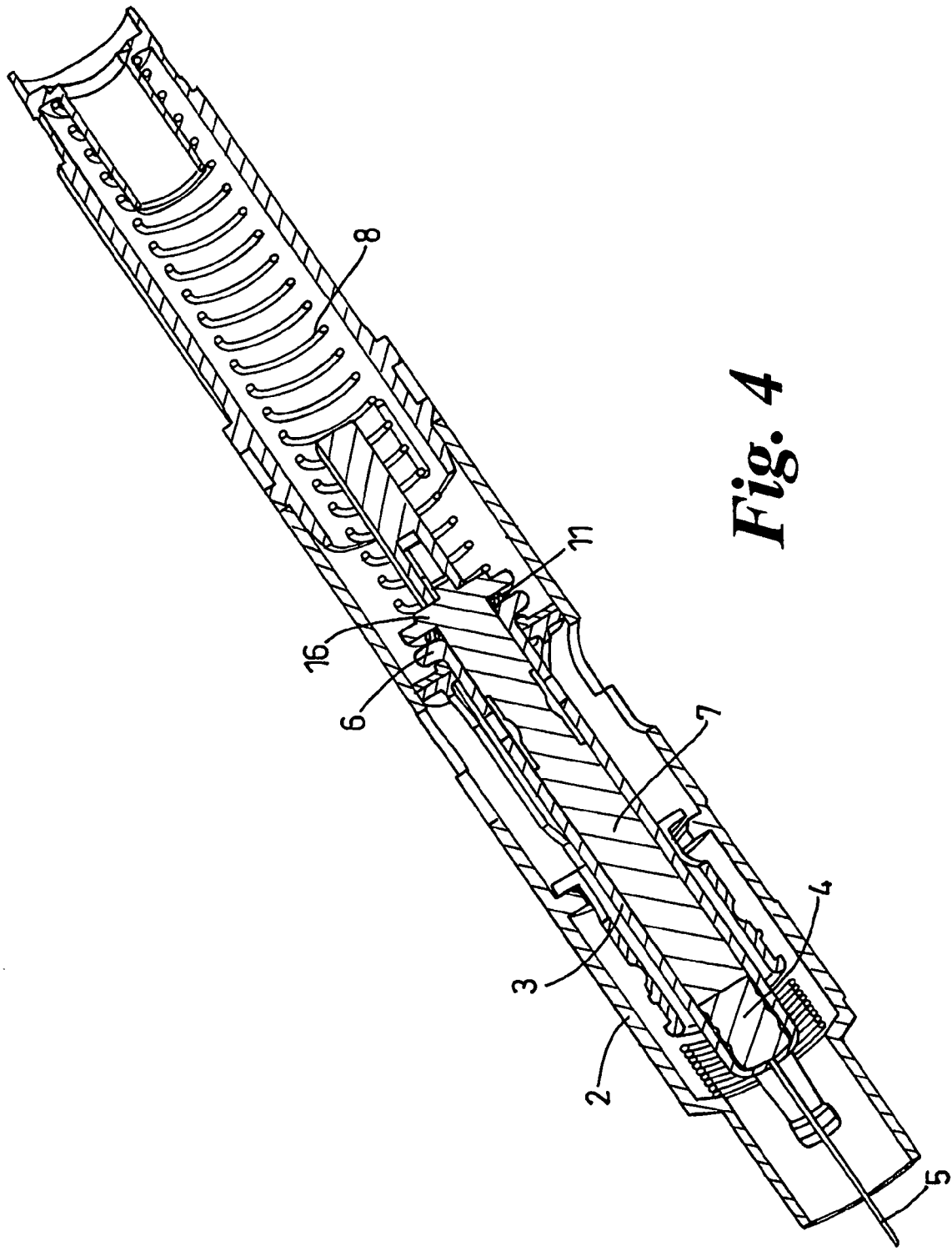

The invention may be performed in various ways and a preferred example thereof will now be described, with reference to the accompanying diagrammatic drawings, in which:

FIG. 1 is a sectional view through an injection device of this invention prior to use; and FIGS. 2 to 4 are similar views showing successive stages of operation of the injection member.

The injection device shown in the drawings comprises a syringe 1 located within a protective housing 2. The syringe comprises a container 3 incorporating a liquid dose held in place by a bung 4 and having a needle 5 through which the dose can be ejected by applying pressure to the bung 4. The container 3 has an enlarged head 6. A plunger 7 is biased forwardly by a coil spring 8, but is held back in a latched position (FIG. 1) until the plunger and the spring 8 are released. Prior to use the syringe 1 is held within the housing 2 by a coil spring 9. The free end 10 of the plunger 7 passes through an O-ring 11 (which creates a tight frictional grip around the plunger) and enters into the top part of the syringe housing 3. In this state, the O-ring 11 rests against the head 6 of the syringe container 3.

When the plunger 7 is released so that the spring 8 pushes it forwardly the frictional force between the plunger 7 and the O-ring 11 causes pressure to be applied to the head of the syringe container 3 to move the syringe bodily forwards (thus compressing spring 9) so that the tip of the needle 5 projects beyond the end of the housing 2, until such time as a ledge 12 on a member 13 connected to the syringe container 3 abuts a stop 14 of the housing 2 (FIG. 2). At this point the syringe can move no further forward, and the end 10 of the plunger 7 is still spaced from the bung 4 by a gap 15. However, the plunger 7 continues its forward movement, under bias of the spring 8, overcoming the frictional force between the plunger and the O-ring 11, and enabling the end 10 of the plunger to contact the bung 4, after closing the gap 15 (as shown in FIG. 3), until the charge has been fully expressed (as shown in FIG. 4).

During the subsequent stage of movement of the plunger 7, there is still a frictional force between the plunger and the O-ring 11 to press the syringe container in a forward direction against the bias of the spring 9 and thus hold the syringe in the desired position with the needle 5 exposed. If desired, the mechanism could be modified to incorporate a bias spring between the head 16 of the plunger 7 and the O-ring 11 which will press the O-ring into firm contact with the head 6 of the syringe container and maintain that forward pressure on the O-ring and the syringe 1 during the injection process. This is shown by way of example in FIG. 3 as the spring 17.

The invention claimed is:

1. An injection device for causing a dose of liquid to be ejected, said device comprising:
   a housing;
   a syringe located within said housing, the syringe comprising a container and a needle at one end of the container through which the dose of liquid is to be ejected;
   a plunger, the syringe being movable by said plunger, upon release of an actuating bias member at one end of the housing, to move the syringe, from a first position wherein the needle is shrouded by the housing, to a second position wherein the needle projects from the housing, the plunger having an end positioned within said container of the syringe; and
   a surrounding and gripping flexible O-ring carried by said plunger, said O-ring rests against an enlarged head of the container, such that a primary movement of the plunger, under a bias of the actuating bias member, transmits a frictional force to the O-ring with the result that the container is moved by and with the O-ring linearly from said first to said second position, whereupon arresting of further movement of the container results in a frictional grip between the plunger and the O-ring being overcome, thus enabling the plunger to move by a secondary movement relatively to the O-ring, further into the container, into contact with and to act upon a plug within the container to compress the dose of liquid within the syringe and cause expression of the dose of liquid through the needle.

2. An injection device as claimed in claim 1, wherein a pressure maintaining bias member is positioned between a head of the plunger and the O-ring to enable pressure to be maintained by the O-ring onto the enlarged head of the container during the secondary movement of the plunger.

3. An injection device as claimed in claim 1, including a return bias member acting between the housing and an other end of the container to hold the syringe retracted within the housing until the actuating bias member is released.

4. An injection device as claimed in claim 1, wherein one or more of the bias members provided within the housing is in the form of a coil spring.

5. An injection device as claimed in claim 2, including a return bias member acting between the housing and an other end of the container to hold the syringe retracted within the housing until the actuating bias member is released.

6. An injection device as claimed in claim 2, wherein one or more of the bias members provided within the housing is in the form of a coil spring.

7. An injection device as claimed in claim 3, wherein one or more of the bias members provided within the housing is in the form of a coil spring.

* * * * *